(12) United States Patent
Sharma et al.

(10) Patent No.: US 6,617,491 B2
(45) Date of Patent: Sep. 9, 2003

(54) USE OF DROSOPHILA MELANOGASTER AS A MODEL FOR SCREENING PSYCHOSTIMULANT PLANT MATERIALS

(75) Inventors: Abhay Sharma, Uttar Pradesh (IN); Amaresh Pandey, Uttar Pradesh (IN); Subhash Singh, Uttar Pradesh (IN); Sushil Kumar, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/789,528

(22) Filed: Feb. 22, 2001

(65) Prior Publication Data

US 2002/0114855 A1 Aug. 22, 2002

(51) Int. Cl.$^7$ .................. G01N 33/00; A01K 67/00; A01K 67/033; C12N 15/00
(52) U.S. Cl. .................. 800/3; 800/8; 800/13; 800/22; 424/725; 424/774
(58) Field of Search .................. 800/3, 8, 22, 13, 800/200; 424/725, 774

(56) References Cited

U.S. PATENT DOCUMENTS 6,291,739 B1 * 9/2001 Sharma et al. .................. 800/3

OTHER PUBLICATIONS

Mehra et al, "Acorus (Araceae)", Pharmacognostic investigations on aconities of "Ferox" group, Res Bull Panjab Univ. 21, 473, pp. 18–23, 1970.

Madan et al, "Anticonvulsant, Antiveratrinic and Antiarrhythmic actions of acorus calamus linn—an indian Indigenous drug", Arch. Int. pharmacodyn. 1960, CXXIV, No. 1–2, pp. 201–211, India Inst. Of Medical Sciences.

Dhalla et al, "Effect of Acorus oil in Vitro on the respiration of rat brain", J. of pharmaceutical sciences, 1961 50:580–582, Lady Harding med. College, New Delhi, India.

Zanoli et al, Sedative and hypothermic effects induced by β–Asarone, a main component of acorus calamus, Phytotherapy research, vol. 12, pp. S114–S116, 1998, John Wiley & Sons , Ltd.

Panchal et al, "Pharmacology of Acorus", Indian J. Exp Biol., 1989, 27:561–567.

Bhakuni et al, "Screening of Indian plants for biological activity*: Part XIII", Indian J. of Experimental Biology vol. 26, 1988, 26:883–904, Central Drug Research Inst., Lucknow, India.

Bhakuni et al, "Screening of Indian plants for biological activity: part II", Indian J. of Experimental biology, 1969 7:250–262, Central Drug Research Inst., Lucknow, India.

Menon et al, "The mechanism of the tranquillizing action of asarone from Acorus calamus Linn", 19:170–175 Dept. of Pharmacology, S.M.S. Medical College, 1966, J. Pharm. Pharmac.

Dandiya et al, "Pharmacological actions of asarone and β–Asarone on central nervous system", Ind. Jour. Med. Res., vol. 50, No. 1, pp. 46–60, 1962 Dept. of Pharmacology.

Sharma et al, "Studies on acorus calamus. Part VI, Pharmacological actions of asarone and β–Asarone on Cardiovascular system and smooth muscles*", Ind. Jour. Med. Res. vol. 50, No. 1, pp. 61–65, 1962, Dept. of Pharmacology, Indian Council of Medical Research.

Chopra et al, "Pharmacological Action of some common essential oil–bearing plants used in indigenous Medicine", Ind. Jour. Med. Res vol. 43, No. 3, 1954, pp. 381–384.

Dhalla et al, "Further studies on neuropharmacological actions of acorus oil", Arch. Int. pharmacodyn., 1968 vol. 172, No. 2, pp. 356–365, Indian Council of medical research, New Delhi.

* cited by examiner

*Primary Examiner*—David Guzo
*Assistant Examiner*—Quang Nguyen
(74) *Attorney, Agent, or Firm*—Foley & Lardner

(57) ABSTRACT

The invention provides a method for screening of plant materials as CNS stimulant/depressant using *Drosophila melanogaster* as a model.

5 Claims, No Drawings

USE OF DROSOPHILA MELANOGASTER AS A MODEL FOR SCREENING PSYCHOSTIMULANT PLANT MATERIALS

FIELD OF THE INVENTION

This invention relates to the identification and use of *Drosophila melanogaster* as a model for screening of plant materials useful as psyhchostimulants.

BACKGROUND OF THE INVENTION

Drugs that stimulate or depress CNS play an important role in human therapeutics. They act as anesthetics, analgesics, sedatives, psychostimulants, analeptics, antidepressants, anticonvulsants etc. and are used in the treatment of conditions such as narcolepsy, depression, hyperactivity disorders, epilepsy and drug addiction in human (Wood-Smith and Stewart, 1964, "Drugs In Anesthetic Practice," Butterworth; Beckman, 1958, "Drugs, Their Nature, Action and Use," W.B. Saunder, Green and Levy, 1976, "Drug Misuse, Human Abuse," Dekker). Undesirable side effects and ineffectiveness of currently available CNS stimulants/depressants in many situations call for development of novel drugs. A variety of CNS active drugs have originated, and many of them are waiting to originate, from plants (Wood-Smith and Stewart, 1964, "Drugs In Anesthetic Practice," Butterworth; Beckman, 1958, "Drugs, Their Nature, Action and Use," W.B. Saunder; Green and Levy, 1976, "Drug Misuse, Human Abuse," Dekker; Plotkin, 2000, "Medicine Quest, In Search of Nature's Healing Secrets," Viking; Gratzar, 2000, Nature 206:235–236). A reason why neuroactive compounds made by plants work on receptors in human brain is also known in the art (Lam et al, 1998, Nature 396:125–126). Keeping the above in view, the applicants used plant materials for screening neuroactive agents.

The applicants recently developed a *Drosophila melanogaster* model for in vivo whole organism based screening of CNS active agents (Sharma and Kumar, a method for screening of central nervous system active agents, U.S. patent application Ser. No. 09/789,525, filed concurrently herewith, the entire disclosure of which is incorporated herein by reference.In particular, the applicant showed that a change in the extent of time required by $Sh^5eag^1$ mutant flies to recover from ether anesthesia could be used as a criterion for rapid screening of CNS stimulant/depressant agents. In the present invention, this fruit fly has been used as a model for screening of plant materials.

The plant material screened and studied by the applicants was an extract obtained from *Acorus calamus*. *Acorus calamus* Linn. is a plant commonly used in Ayurvedic medicine. Its roots and rhizomes are used in various ailments, including many mental disorders, such as hysteria, insanity, insomnia, melancholia, neurasthenia, epilepsy, diarrhoea and asthma (Nadkarni, 1927, The Indian materia medica, Bombay, 26; Kirtikar and Basu, 1933, Indian medicinal plants, vol. IV, Lalit Mohan Basu, Allahabad, p.2626). The common Indian names of the plant are Ugargandha (Saskrit), ghor bach (Hindi), Bacha (Urdu), Wasa (Telugu) and Sweet flag (English).

Modern studies on the neuropharmacological actions of *Acorus calamus* have demonstrated CNS activity in roots and rhizomes, not leaves, of the plant (Bhakuni et al, 1988, Ind. J. Exp. Biol. 26:883–904; Bhakuni et al, 1969, Ind. J. Exp. Biol., 7:250–262). Mainly, CNS depressant actions of *Acorus calamus* have been reported (Zanoli et al, 1998, Phytother, Res. 12:S114–S116; Panchal et al, 1989, Ind. J. Exp. Biol. 27:561–567; Dandiya and Sharma, 1962, Ind. J. Med. Res. 50:46–60; Chopra et al, 1954, Ind. J. Med. Res. 42:381384; Menon and Dandiya, 1966, J. Pharm, Pharmac. 19:170–175; Dhalla et al, 1961, J. Pharmaceut. Sci. 50:580–582; Dhalla and Bhattacharya, 1968, Arch. Int. Pharmacodyn. 172:356–365; Madan et al, 1960; CXXIV:201–211; Dandiya and Menon, 1965, Life Sci. 4:1635–1641).

The active principles identified are asarone and β-asarone, obtained from roots and rhizomes after steam distillation of volatile oil. Various workers have mainly characterized as having CNS depressant actions such as sedative, tranquilizing, hypnosis potentiation, anticonvulsant, spontaneous motor activity antagonizing, amphetamine induced hyperactivity, antagonizing and analgesic activities to roots and rhizomes of *Acorus calamus*.

A CNS stimulant action of the oil from the plant has been reported by Chopra et al, 1954, md. J. Med. Res., 42:381–384). The authors have however given no proof in support of their statement. It is possible that the generalized convulsions induced by β-asarone might have made these workers ascibe a stimulant property to *Acorus calamus* (Panchal and Venkatkrishna-Bhatt, 1989, Ind. J. Exp. Biol. 27:561–567; Dandiya and Sharma, 1962, Ind. J. Med. Res., 50:46–60). In addition, based on the studies related to the effect of asarone on the learned behaviour of the rats it has been suggested that the substance may cause a stimulant action at a higher dose and depression at a lower dosage (Dandiya and Sharma, 1962, Ind .J. Med. Res., 50:46–60).

Thus, in the prior art, only roots and rhizomes, not leaves, of *Acorus calamus* are known to possess drug-like activities. Also, the known neuroactivities, of the plant are limited to actions such as sedation, tranquilizing, hypnosis potentiation and convulsions.

Therefore, the extract obtained from the leaves of this plant was screened for CNS stimulant/depressant activity. The Applicants, to their surprise found that the extract works as an excellent CNS stimulant/depressant.

OBJECTS OF THE INVENTION

The main object of the invention is to provide a method whereby plant materials can be screened to test their efficacy as CNS depressant/stimulants.

Another object of the invention is to provide a method for treatment of poisoning, narcolepsy, depression, hyperactivity disorders, alcohol/drug addiction etc. in humans.

SUMMARY OF THE INVENTION

The invention provides a method for screening of plant materials as CNS stimulant/depressant using *Drosophila melanogaster* as a model.

DETAILED DESCRIPTION OF THE INVENTION

Accordingly, the invention provides a novel method whereby plant materials can be screened for their efficacy as CNS stimulant/depressants. The extract of several plants including *Acorus calamus* was tested for CNS stimulation/depression activity in the mutant fruit fly *Drosophila melanogaster* $Sh^5eag^1$.

The invention provides a method for the detection of the analeptic and psychostimulant properties of extract obtained from *Acorus calamus,* using *Drosophila melanogaster* $Sh^5eag^1$ said method comprising the steps of:

(a) preparing acetone and methanol extracts of leaves of the plant *Acorus calamus*, (b) treating $Sh^5eag^1$ *Drosophila melanogaster* mutant flies in the media selected from normal fly food, normal food mixed with phenobarbital, normal food mixed with ethanol, normal food mixed with the alcoholic sample prepared above, normal food mixed with both the alcoholic sample prepared above and phenobarbital and normal food mixed with both the alcoholic sample of step (a) and ethanol, (c) subjecting differently treated flies to ether anesthesia and then determining extent of time required by them to recover, (d) observing spontaneous locomotor activity in the differently treated flies and increase in the spontaneous locomotor activity is indicative of analeptic activity of extract of *Acorus calamus* against ethanol, (e) Observing the recovery time following ether and chloroform anesthesia in flies not pretreated with phenobarbital wherein quick recovery of the flies is indicative of analeptic activity of the extract against phenobarbital, (f) Observing the recovery time in flies anesthetized with ether and pretreated with phenobarbital, wherein quick recovery of the flies is indicative of analeptic activity of the extract, (g) observing the spontaneous locomotor activity of the flies under the influence of ethanol, wherein quick recovery of the flies is indicative of analeptic activity of the extract and (h) observing the spontaneous locomotor activity of the flies not under the influence of ethanol, wherein quick recovery of the flies is indicative of the psychostimulant activity of the extract.

In an embodiment, the extract of *Acorus calamus* is directly used or used as a source of an analeptic, a psychostimulant, an antidepressant, an antabuse and a somnolytic.

In another embodiment, the extract of *Acorus calamus* is directly used or used as a source of a therapeutic agent to treat depressant poisoning, narcolepsy, depression, hyperactivity disorders and alcohol/drug addiction in humans.

Using a fruit fly model, more than 20 plant species were tested for neuroactive agents. Extracts of the plant *Acorus calamus* were found to decrease the time taken by flies to recover from anesthesia, a state of severe CNS depression, produced by diethyl ether. Further experiments with one of the *Acorus calamus* extracts showed a similar effect on flies anesthetized with chloroform. Also, the extract suppressed delay in recovery from ether anesthesia caused by CNS depressant drug phenobarbital. In addition, the inhibition in flies' spontaneous locomotor activity caused by ethanol, an another CNS depressant, was also suppressed. The above results therefore demonstrate that the natural substance screened has a property akin to known analeptics, drugs and antagonize the action of CNS depressants. The plant extract was also found to increase spontaneous locomotor activity, an expression of CNS activity status, in normal flies. This further suggests that the agent also possess a property similar to known psychostimulants. Accordingly, the present invention provides a substance from *Acorus calamus* plant with analeptic and psychostimulant properties which comprises use of a Drosophila model for in vivo drug screening, testing of a large number of plant extracts from various plant species and finding in the plant *Acorus calamus* a substance with analeptic and psychostimulant properties.

The invention is illustrated by the following examples, which are provided to illustrate the invention and should not be construed as limitation on the inventive concept herein.

EXAMPLE 1

Standard Drosophila manipulation methods were followed. Cultures were grown on a medium containing maize powder, sugar, yeast and Nipagin. Flies were maintained and further manipulated at room temperature. Experimental conditions were kept identical throughout. The double mutant $Sh^5eag^1$ was generated using standard methods of Drosophila genetics. Male flies of similar age were used in the experiment. In routine screening, flies were anesthetized in various groups and then allowed to recover in an identical manner. For further testing, individual fly pairs were used as described below. Following different treatments, flies were first anesthetized with diethyl ether and healthy looking individuals shifted to a number of empty vials in such a way that each vial received two flies, one from each treatment. Before shifting, flies from one of the two treatments were marked on their wings for the purpose of identification. Flies were allowed to recover fully. After an hour, each fly pair was subjected to the following test. The two flies, inside a vial with 800 mg of cotton plug, were simultaneously anesthetized by pouring 0.2 ml of diethyl ether on to the plug. After about 1.5 min, during which the vial was gently shaken continuously so that the flies remained at the bottom throughout, the two individuals were immediately shifted to two empty vials. Time at this point was considered 0 min. Etherisation caused the flies to become completely immobile and be on their back. Care was taken to leave the flies in similar position in both the vials. Flies were now constantly watched very carefully. As soon as a fly stood up on its legs, time past 0 min was recovered in min, after rounding off. This time was considered to represent recovery time.

EXAMPLE 2

Around 200 plant extracts, representing different parts of more than 20 plant species, were prepared using solvents such as hexane, chloroform, acetone, methanol and ethanol as extraction media. The plant parts were dried, ground and soaked sequentially in various solvents, in the order given above, at room temperature. The plant materials were soaked in a particular solvent for 3 days, each day the treated solvent being recovered and replaced with fresh solvent. The three batches of the treated solvents were then pooled together. The extracts were finally obtained by steam distillation followed by evaporation at 37° C. of the remaining solvent. The samples were uniquely coded and stored at 10° C. till further use.

EXAMPLE 3

A blind screening of coded plant extracts was performed in the following manner. Extracts were dissolved in ethanol at a concentration of 40–50 mg/ml. Either freshly prepared alcoholic samples or ethanol alone were thoroughly mixed, 5% (v/v), in melted fly medium mentioned earlier. The media so prepared was poured in 25×100 mm glass vials, 2–3 ml each. The media was allowed to solidify at room temperature, before being kept at 10° C. overnight. Vials were brought to room temperature and then 15–20 $Sh^5eag^1$ male flies were shifted to each vial. Drosophila culture conditions and fly manipulation methods used were as described earlier. At least two replicates were set up for each of the two treatments namely, normal food (NF) and normal food with extract (NF+EX). The vials containing flies were kept in an inverted position, with medium at the top and cotton plug at the bottom, for 5–6 days at room temperature. Two groups, one from NF and the other from NF+EX treatment, of 10–12 flies each were etherized and then allowed to recover in parallel in two vials under extractly identical conditions. Flies were observed to see if NF+EX treated ones tend to recover earlier or later than those treated with NF. Two replicates were similarly examined.

The above screening resulted in the detection of 2 extracts that appeared to delay recovery from ether anesthesia in flies. Acetone and methanol extracts of leaves of the plant *Acorus calamus* were the ones which tested positive. The absence of activity in other Acorus extracts was although not confirmed. The test with acetone and methanol extracts, blind with respect to control and extract treatment in flies, was repeated several times and each time the activity of the two extracts were confirmed. In an experiment, for example, acetone extract treated flies were found to revive earlier than control flies in all the 15 consequent tests conducted. Similarly, methanol extract tested positive in all the 10 consequent tests were carried out.

To understand the above activity, and others, if any, of the Acorus extracts in Drosophila in a quantitative manner, following experiments were carried out using acetone extract as the representative substance. In all the experiments that follow, parallel sets of control and, extract and/or drug treated flies were used. The extract's concentration in fly medium was kept same as mentioned earlier. First, time of recovery from ether anesthesia was measured in individual flies. Flies were cultured, handled and treated as described earlier. A pair of fly, one each from NF and NF+EX, was simultaneously anesthetized and allowed to recover from anesthesia. Following this, recovery time was determined as described earlier. A total of 22 fly pairs were examined. The recovery time of NF and NF+EX flies were found to be 5.36±0.61 and 3.72±0.94 minutes respectively. Although the difference (p>0.1) did not attain significance, a quicker recovery in extract treated flies was nevertheless observed. The above experiment demonstrates an analeptic action of the Acorus substance.

To know if the effect of the plant extract on recovery from anesthesia is anaesthetic agent specific, chloroform instead of diethyl ether was used in a similar experiment. For producing anesthesia, 0.05 ml of chloroform, as against 0.1 ml of diethyl ether, was applied. A total of 25 fly pairs were examined. The recover time obtained for NF and NF+EX flies were 13.04±2.11 and 8.96±1.51 minutes respectively. Although the difference failed to achieve significance (p>0.1), a faster recovery in extract treated flies was evident. This demonstrates that the extract has an analeptic activity also against chloroform.

Sedative-hypnotic drug phenobarbital sodium (PS) causes a delay in recovery from ether anesthesia in flies (Sharma and Kumar, a method for screening of central nervous system active agents, loc. cit., Ser. No. 09/789,525. To understand if this delayed recovery is affected by Acorus extract, recovery time in NF+PS and NF+PS+EX treated flies were determined. The concentration of PS in the fly food was 1 mg/ml. Other conditions were as described earlier. A total of 10 fly pairs were examined. The recovery time obtained was 11.3±2.38 and 7.5±1.49 minutes respectively. Although the difference was not significant (p>0.1), a quicker recovery in extract treated flies was nevertheless observed. This indicates that the extract might have an analeptic activity also against phenobarbital.

To further understand the activity profile of the plant material, flies were treated with either NF or NF containing either ethanol alone (NF+ET) or ethanol and extract both (NF+ET+EX). The ethanol concentration used was 20% (v/v). Other details were as described earlier. On 5th day, spontaneous locomotor activity in flies was pair-wise compared either between NF and NF+ET or between NF+ET and NF+ET+EX. Two vials representing the two treatments were kept side by side in an inverted position. There were 20 flies in each vial. The flies' activity in a group was visually estimated on a scale of '0', '+' or '−', as described below. To compare between NF and NF+ET, the sum total of activity seen in the vial containing NF flies was considered '0'. The activity in the NF+ET vial was then given a '0', '+' or '−', depending on whether it is equal, more or less than the activity observed in NF vial respectively. The process was repeated 73 times spanning an entire day. In this test, ethanol treated flies received 23 '0's, no '+' and 50 '−'s. In other words, NF+ET flies were found to be 23 times equally active, no time more active and 50 times less active than NF flies. NF+

ET and NF+ET+EX flies were similarly compared, with the activity in the former serving as baseline, i.e., '0'. In this test, NF+ET+EX received no '0', 73 '+'5 and no '−'. In other words, flies treated with ethanol and extract both were found to be all the time more active than those treated with ethanol alone. The above experiments demonstrate two things. First, ethanol decreases spontaneous locomotor activity in flies. Second, Acorus extract increases spontaneous locomotor activity in flies treated with ethanol, a CNS depressant drug. This suggests that the Acorus extract has an analeptic action also against ethanol.

Having observed a stimulant activity of Acorus extract in flies under the influence of alcohol, the question whether the extract also stimulates normal flies, i.e., individuals not under the drug's influence, was asked. To answer this, spontaneous locomotor activity in NF and NF+EX flies were compared, as described above. NF flies' activity served as the baseline. In the test conducted the extract treated flies received 18 '0'5 53 '−'5 and 2 '−'s. In other words, NF+EX treated flies were 18 times equally active, 53 times more active and 2 times less active than NF treated ones. This indicated that the Acorus extract also has a psychostimulant property.

We have described here a neuroactive substance that is derived from *Acorus calamus* leaves and which exhibits analeptic and psychostimulant properties. The novelty of our invention is ascertained by scanning the literature on the therapeutic attributes of the plant.

Advantages of the Invention

1. As fruit fly is amenable to genetic and molecular analysis, the neuroactivity of the substance detected can be further studied directly in this organism
2. The analeptic substance described here can serve as a tool in studies pertaining to anesthesia. This is all the more important considering the status of Drosophila as an anesthesia model.
3. Because the substance screened has a broad spectrum of CNS activity, it has the potential to be directly used as, or to be developed in to agents such as, an analeptic, an antidepressant, an antabuse, a somnolytic and a psychostimulant. The substance may therefore be potentially used in the treatment of depressant poisoning, narcolepsy, depression, hyperactivity disorders, alcohol/drug addiction etc. in human.
4. Since the drug-like substance screened is a plant product, the invention provides a boost to bioprospection and biodiversity conservation.

What is claimed is:

1. A method for detection of the psychostimulant properties of an extract obtained from the plant *Acorus calamus*, using mutant fruit fly Drosophila melanogaster $Sh^5$ $eag^1$, said method comprising:
   (a) preparing an acetone and/or methanol extract of leaves from the plant,
   (b) treating the mutant fruit flies, with normal fly food or normal fly food mixed with the extract of(a), and
   (c) observing the change in the spontaneous locomotor activity of the differently treated flies of (b), wherein an increase in the spontaneous locomotor activity in flies treated with normal fly food with the extract of (a), compared to flies treated with normal fly food, is indicative of the pyschostimulant property of the extract.

2. An analeptic and psychostimulant composition, wherein said composition comprises an acetone and/or methanol extract from leaves of *Acorus calamus*.

3. A method for detection of the analeptic property of an extract obtained from the plant *Acorus calamus*, using mutant fruit fly Drosophila melanogaster $Sh^5$ $eag^1$, said method comprising:
   (a) preparing an acetone and/or methanol extract of leaves from the plant,
   (b) treating the mutant fruit flies, with fly food mixed with a depressant drug in the absence or presence of the extract of(a), and
   (c) observing the change in the spontaneous locomotor activity of the differently treated flies of (b), wherein an increase in the spontaneous locomotor activity in flies treated with fly food mixed with a depressant drug in the presence of the extract, compared to flies treated with fly food mixed with a depressant drug in the absence of the extract, is indicative of the analeptic property of the extract.

4. A method for detection of the analeptic property of an extract obtained from the plant *Acorus calamus*, using mutant fruit fly Drosophila melanogaster $Sh^5$ $eag^1$, said method comprising:
   (a) preparing an acetone and/or methanol extract of leaves from the plant,
   (b) treating the mutant fruit flies, with fly food mixed with a depressant drug in the absence or presence of the extract of (a),
   (c) exposing the differently treated flies of (b) to anesthesia, and
   (d) observing the time taken by the flies of (c) to recover from anesthesia, wherein the decrease in arousal time in flies treated with normal fly food mixed with the extract, compared to flies treated with normal fly food, is indicative of the analeptic property of the extract.

5. The method as claimed in claim 4, wherein the anesthesia is selected from a group consisting of ether, chloroform, ethanol, and Phenobarbital.

* * * * *